(12) United States Patent
Bankiewicz

(10) Patent No.: US 9,089,667 B2
(45) Date of Patent: Jul. 28, 2015

(54) REFLUX RESISTANT CANNULA AND SYSTEM FOR CHRONIC DELIVERY OF THERAPEUTIC AGENTS USING CONVECTION-ENHANCED DELIVERY

(75) Inventor: Krystof S. Bankiewicz, Oakland, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1112 days.

(21) Appl. No.: 11/507,939

(22) Filed: Aug. 21, 2006

(65) Prior Publication Data

US 2007/0088295 A1 Apr. 19, 2007

Related U.S. Application Data

(60) Provisional application No. 60/710,770, filed on Aug. 23, 2005.

(51) Int. Cl.
*A61M 5/00* (2006.01)
*A61M 25/00* (2006.01)
*A61M 25/06* (2006.01)
*A61M 25/02* (2006.01)

(52) U.S. Cl.
CPC ....... *A61M 25/0023* (2013.01); *A61M 25/0606* (2013.01); *A61M 25/0662* (2013.01); *A61M 25/02* (2013.01); *A61M 2025/028* (2013.01); *A61M 2025/0286* (2013.01); *A61M 2025/0681* (2013.01); *A61M 2210/0693* (2013.01)

(58) Field of Classification Search
CPC ............... A61M 25/0068; A61M 25/0041; A61M 25/0043; A61M 25/0069; A61M 2025/0073; A61M 25/008; A61M 2025/0042; A61M 25/0023; A61M 25/02; A61M 25/0606; A61M 25/0662; A61M 2025/028; A61M 2025/0286; A61M 2025/0681; A61M 2210/0693
USPC ............. 604/523–532, 93.01, 506, 151, 158, 604/164.01, 164.11, 264, 272
See application file for complete search history.

(56) References Cited

U.S. PATENT DOCUMENTS

| | | | |
|---|---|---|---|
| 4,149,535 A | 4/1979 | Volder | |
| 4,239,042 A | 12/1980 | Asai | |

(Continued)

FOREIGN PATENT DOCUMENTS

| | | |
|---|---|---|
| EP | 1491154 | 12/2004 |
| GB | 1255551 A | 12/1971 |

(Continued)

OTHER PUBLICATIONS

Bankiewicz; et al., "Practical Aspects of the Development of ex Vivo and in Vivo Gene Therapy for Parkinson's Disease", Experimental Neurology (1997) 144:147-156.

(Continued)

*Primary Examiner* — Aarti B Berdichevsky
*Assistant Examiner* — Laura Schell
(74) *Attorney, Agent, or Firm* — Bozicevic, Field & Francis LLP; Pamela J. Sherwood

(57) ABSTRACT

A step-design cannula and delivery system for chronic delivery of therapeutic substances into the brain using convention-enhanced delivery of therapeutic substances and which effectively prevents reflux in vivo and maximizes distribution in the brain.

14 Claims, 14 Drawing Sheets

(56) References Cited

U.S. PATENT DOCUMENTS

| | | | |
|---|---|---|---|
| 4,335,718 | A | 6/1982 | Calabrese |
| 4,449,532 | A | 5/1984 | Storz |
| 4,543,092 | A | 9/1985 | Mehler et al. |
| 4,597,421 | A | 7/1986 | Wells |
| 4,629,450 | A | 12/1986 | Suzuki et al. |
| 4,738,658 | A | 4/1988 | Magro et al. |
| 4,739,768 | A | 4/1988 | Engelson |
| 4,781,691 | A | 11/1988 | Gross |
| 4,909,800 | A | 3/1990 | Gross |
| 4,978,334 | A | 12/1990 | Toye et al. |
| 5,069,673 | A | 12/1991 | Shwab |
| 5,256,157 | A | 10/1993 | Samiotes et al. |
| 5,593,393 | A | 1/1997 | Trudell et al. |
| 5,720,720 | A | 2/1998 | Laske et al. |
| 5,851,203 | A | 12/1998 | Van Muiden |
| 5,902,282 | A | 5/1999 | Balbierz |
| 5,919,171 | A | 7/1999 | Kira et al. |
| 6,020,196 | A | 2/2000 | Hu et al. |
| 6,026,316 | A | 2/2000 | Kucharczyk et al. |
| 6,030,369 | A | 2/2000 | Engelson et al. |
| 6,042,579 | A | 3/2000 | Elsberry |
| 6,186,986 | B1 | 2/2001 | Berg et al. |
| 6,210,392 | B1 | 4/2001 | Vigil et al. |
| RE37,410 | E | 10/2001 | Brem |
| 6,309,634 | B1 | 10/2001 | Bankiewicz et al. |
| 6,458,088 | B1 | 10/2002 | Hurtak et al. |
| 6,524,299 | B1 | 2/2003 | Tran et al. |
| 6,533,751 | B2 | 3/2003 | Cragg et al. |
| 6,641,564 | B1 | 11/2003 | Kraus |
| 6,663,606 | B1 | 12/2003 | Barry et al. |
| 7,037,295 | B2 | 5/2006 | Tiernan et al. |
| 7,182,944 | B2 | 2/2007 | Bankiewicz |
| 7,815,623 | B2 | 10/2010 | Bankiewicz et al. |
| 8,337,458 | B2 | 12/2012 | Bankiewicz et al. |
| 2002/0087152 | A1 | 7/2002 | Mikus et al. |
| 2002/0091372 | A1 | 7/2002 | Cragg et al. |
| 2002/0095081 | A1 | 7/2002 | Vilsmeier |
| 2002/0114780 | A1 | 8/2002 | Bankiewicz et al. |
| 2002/0141980 | A1 | 10/2002 | Bankiewicz et al. |
| 2003/0073934 | A1 | 4/2003 | Putz |
| 2003/0216714 | A1 | 11/2003 | Gill |
| 2004/0092879 | A1* | 5/2004 | Kraus et al. ............ 604/158 |
| 2004/0209810 | A1 | 10/2004 | Gill et al. |
| 2004/0215162 | A1* | 10/2004 | Putz ....................... 604/500 |
| 2005/0112065 | A1 | 5/2005 | Drummond et al. |
| 2005/0154297 | A1 | 7/2005 | Gill |
| 2005/0256503 | A1 | 11/2005 | Hall |
| 2006/0073101 | A1 | 4/2006 | Oldfield et al. |
| 2006/0073119 | A1 | 4/2006 | Forsayeth et al. |
| 2006/0129126 | A1 | 6/2006 | Kaplitt et al. |
| 2006/0135945 | A1* | 6/2006 | Bankiewicz et al. ......... 604/506 |
| 2006/0217664 | A1 | 9/2006 | Hattler et al. |
| 2007/0110798 | A1 | 5/2007 | Drummond et al. |
| 2007/0250021 | A1* | 10/2007 | Brimhall et al. ............. 604/264 |
| 2007/0254842 | A1 | 11/2007 | Bankiewicz |
| 2008/0228168 | A1 | 9/2008 | Mittermeyer et al. |
| 2009/0088695 | A1 | 4/2009 | Kapur et al. |
| 2009/0088730 | A1 | 4/2009 | Hoofnagle et al. |
| 2009/0143764 | A1 | 6/2009 | Nelson |
| 2009/0198218 | A1 | 8/2009 | Gill |

FOREIGN PATENT DOCUMENTS

| | | |
|---|---|---|
| JP | 2002-509767 | 4/2002 |
| WO | 95/13843 | 5/1995 |
| WO | 99/04849 | 2/1999 |
| WO | WO 99/49909 | 10/1999 |
| WO | 01/30403 | 5/2001 |
| WO | 02/053205 A2 | 7/2002 |
| WO | 2004/031348 | 4/2004 |

OTHER PUBLICATIONS

Bankiewicz; et al., "Focal striatal dopamine may potentiate dyskinesias in parkinsonian monkeys", Exp Neurol (2005) 197:363-372.

Bankiewicz: et al., "Convection-enhanced delivery of AAV vector in parkinsonian monkeys; in vivo detection of gene expression and restoration of dopaminergic function using pro-drug approach", Exp Neurol (2000) 164(1):2-14.

Bruce; et al., "Intracerebral clysis in a rat glioma model", Neurosurgery (2000) 46(3):683-91.

Chen; et al., "Combination Therapy with Irinotecan and Protein Kinase C Inhibitors in Malignant Glioma", Cancer, (2003) 97(9 Suppl):2363-2373.

Chen; et al., "Surface properties, more than size, limiting convective distribution of virus-sized particles and viruses in the central nervous system", J. Neurosurg. (2005) 103: 311-319.

Chen; et al., "Variables affecting convection-enhanced delivery to the striatum: a systematic examination of rate of infusion, cannula size, infusate concentration, and tissue-cannula sealing time", J Neurosurg (1999) 90(2):315-20.

Cunningham; et al., "Distribution of AAV-TK following intracranial convection-enhanced delivery into rats", Cell Transplant (2000) 9(5):585-94.

Groothuis, "The blood-brain and blood-tumor barriers: a review of strategies for increasing drug delivery", Neuro-oncol (2000) 2 (1):45-59.

Hadaczek; et al., "Convection-Enhanced Delivery of Adeno-Associated Virus Type 2 (AAV2) into the Striatum and Transport of AAV2 within Monkey Brain", Human Gene Therapy (2006) 17:1-12.

Hadaczek; et al., "The "Perivascular Pump" Driven by Arterial Pulsation is a Powerful Mechanism for the Distribution of Therapeutic Molecules within the Brain", Mol Ther. (2006) 14(1):69-78.

Hadaczek; et al., ""Perivascular pump" driven by arterial pulsation is a powerful mechanism for the distribution of therapeutic molecules within the brain", Molecular Therapy 2006b; in press.

Haroun; et al., "Local drug delivery", Current Opinion in Oncology (2000) 12:187-193.

Krauze; et al., "Effects of the perivascular space on convection-enhanced delivery of liposomes in primate putamen", Experimental Neurology, (2005) 196:104-111.

Krauze et al., "Reflux-free cannula for convection-enhanced high-speed delivery of therapeutic agents", J. Neurosurg., (2005) 103:923-929.

Krauze et al., "Real-time Imaging and Quantification of Brain Delivery of Liposomes", Pharmaceutical Research (2006) 23: 2493-2504.

Laske; et al., "Chronic interstitial infusion of protein to primate brain: determination of drug distribution and clearance with single-photon emission computerized tomography imaging", J Neurosurg (1997) 87(4):586-94.

Lonser; et al., "Successful and safe perfusion of the primate brainstem: in vivo magnetic resonance imaging of macromolecular distribution during infusion", J Neurosurg (2002) 97(4):905-13.

Mamot; et al., "Extensive distribution of liposomes in rodent brains and brain tumors following convection-enhanced delivery", J Neurooncol (2004) 68(1):1-9.

Mardor; et al., "Monitoring response to convection-enhanced taxol delivery in brain tumor patients using diffusion-weighted magnetic resonance imaging", Cancer Res (2001) 61(13):4971-3.

Morrison; et al., "High-flow microinfusion: tissue penetration and pharmacodynamics", Am J Physiol.(1994) 266(1 Pt 2):R292-305.

Morrison; et al., "Focal delivery during direct infusion to brain: role of flow rate, catheter diameter, and tissue mechanics", Am. J. Physiol. Regul. Integr. Comp. Physiol. (1999) 277:1218-1229.

Nicholson, et al., "Extracellular space structure revealed by diffusion analysis", Trends Neurosci (1998) 21:207-15.

Pardridge, "Drug Delivery to the Brain", J Cereb Blood Flow Metab (1997) 17:713-731.

Pardridge, "The Blood-Brain Barrier: Bottleneck in Brain Drug Development", NeuroRx (2005) 2:3-14.

Patel et al., "Intraputamenal Infusion of Glial Cell Line-Derived Neurotrophic Factor in PD: A Two-Year Outcome Study", Ann. Neurol., (2005) 57:298-302.

(56) References Cited

OTHER PUBLICATIONS

Saito; et al., "Distribution of Liposomes into Brain and Rat Brain Tumor Models by Convection-Enhanced Delivery Monitored wih Magnetic Resonance Imaging", Cancer Research, (2004) 64:2572-2579.

Saito; et al., "Convection-enhanced delivery of tumor necrosis factor-related apoptosis-inducing ligand with systemic administration of temozolomide prolongs survival in an intracranial glioblastoma xenograft model", Cancer Res (2004b) 64(19):6858-62.

Saito; et al., "Gadolinium-loaded liposomes allow for real-time magnetic resonance imaging of convection-enhanced delivery in the primate brain", Exp Neurol (2005) 196(2):381-9.

Vogelbaum, J., "Convection enhanced delivery for the treatment of malignant gliomas: symposium review", Neuro-Oncology (2005) 73:57-69.

Westphal; et al., "Perspectives of cellular and molecular neurosurgery", J Neurooncol (2004) 70(2):255-69.

Lieberman et al., "Convection-enhanced distribution of large molecules in gray matter during interstitial drug infusion," (1995) J. Neurosurg. 82(6):1021-9.

Marshall et al., "Biocompatibility of cardiovascular gene delivery catheters wtih adenovirus vectors: an important determinant of the efficiency of cardiovascular gene transfer," (2000) Mol. Ther. 1(5 Pt 1):423-9.

Naimark et al., "Adenovirus-catheter compatibility increases gene expression after delivery to porcinemyocardium," (2003) Hum. Gene Ther. 14(2):161-6.

Quereshi et al., "Multicolumn Infusion of Gene Therapy Cells into Human Brain Tumors: Technical Report," (2000) Neurosurgery 46(3):663-9.

Tsui et al., "Stability of adenoviral vectors following catheter delivery," (2001) Mol. Ther. 3(1):122-5.

Yin, et al., "Optimal Region Of The Putamen For Image-Guided Convection-Enhanced Delivery Of Therapeutics in Human And Non-Human Primates," NeuroImage Epublication, pp. 1-8 (2009).

\* cited by examiner

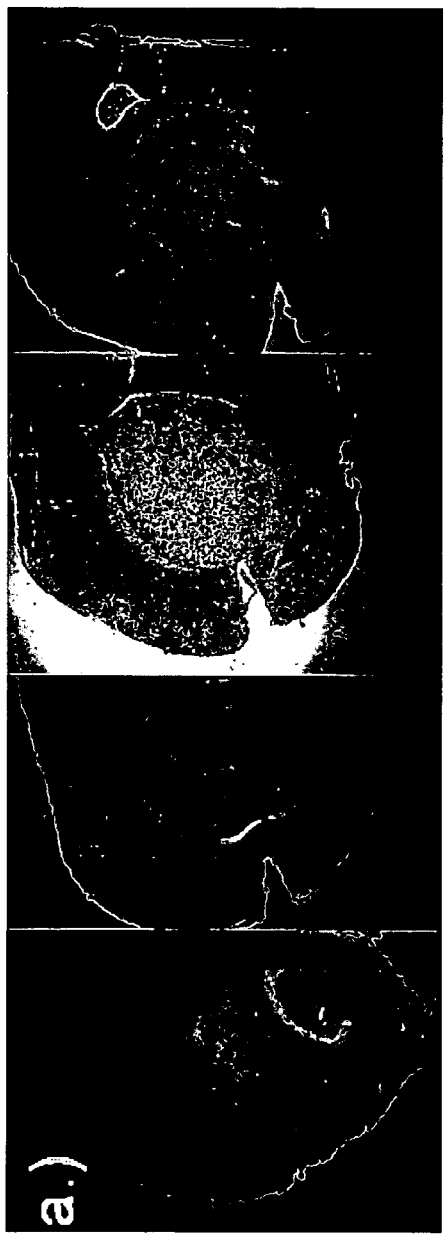
FIG. 11A  FIG. 11B  FIG. 11C  FIG. 11D
FIG. 12A  FIG. 12B  FIG. 12C  FIG. 12D

REFLUX RESISTANT CANNULA AND SYSTEM FOR CHRONIC DELIVERY OF THERAPEUTIC AGENTS USING CONVECTION-ENHANCED DELIVERY

CROSS-REFERENCE TO RELATED APPLICATIONS

This application claims priority to provisional U.S. application No. 60/710,770, filed on Aug. 23, 2005, incorporated herein by reference in its entirety.

This application is related to U.S. Patent Application Publication Number US 2006/0135945 A1, filed on Oct. 5, 2005, and published on Jun. 22, 2006, incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

Incorporation by Reference

The following publications, which are referred to herein using numeric identifiers (e.g., (1)), are incorporated herein by reference in their entirety.

1. Bankiewicz K S, Eberling J L, Kohutnicka M, et al.: Convection-enhanced delivery of AAV vector in parkinsonian monkeys; in vivo detection of gene expression and restoration of dopaminergic function using pro-drug approach. Exp Neurol. 164:2-14, 2000.
2. Bobo R H, Laske D W, Oldfield E H, et al: Free in PMC Convection-enhanced delivery of macromolecules in the brain. Proc Natl. Acad. Sci. USA 91:2076-80, 1994.
3. Bruce J N, Falavigna A, Parsa A T, et al: Intracerebral Clysis in a Rat Glioma Model. Neuro surgery 46:683-691, 2000.
4. Chen Z J, Broaddus W C, Gillies G T, et al: Inraparenchymal drug delivery via positive-pressure infusion: experimental and modeling studies of poroelasticity in brain phantom gels. IEEE Transactions on biomedical engineering, 49:85-96, 2002.
5. Chen Z J, Gillies G T, Broaddus W C, et al.: A realistic brain tissue phantom for intraparenchymal infusion studies. J Neurosurg 101:314-322, 2004.
6. Cunningham J, Oiwa Y, Nagy D, et al.: Distribution of AAV-TK following intracranial convection-enhanced delivery into rats. Cell Transplant. 9:585-94, 2000.
7. Degen J W, Walbridge S, Vortmeyer A O, et al: Safety and efficacy of convection-enhanced delivery of gemcitabine or carboplatin in a malignant glioma model in rats. J Neurosurg. 99:893-898, 2003.
8. Hamilton J F, Morrison P F, Chen M Y, et al: Heparin coinfusion during convection-enhanced delivery (CED) increases the distribution of the glial-derived neurotrophic factor (GDNF) ligand family in rat striatum and enhances the pharmacological activity of neurturin. Exp Neurol 168:155-161, 2001.
9. Johnson E M, Berk D A, Dean W M. et al.: Diffusion and partitioning of proteins in charged agarose gels. Biophys J 68:1561-1568, 1995.
10. Kroll R A, Pagel M A, Muldoon L L, et al: Increasing Volume of Distribution t the Brain with Interstitial Infusion: Dose, Rather Than Convection, Might be the Most important factor. Neurosurgery 38:746-754, 1996.
11. Kunwar S: Convection enhanced delivery of IL-13-PE38QQR for treatment of recurrent malignant glioma: presentation of interim findings from ongoing phase 1 studies. Acta Neurochir 88:105-111, 2003.
12. Lidar Z, Mardor Y, Jonas T, et al: Convection-enhanced delivery of paclitaxel for the treatment of recurrent malignant glioma: a phase I/II clinical study. J Neurosurg. 100:472-479, 2004.
13. Lonser R R, Walbridge S, Oldfield E H, et al: Successful and safe perfusion of the primate brainstem: in vivo magnetic resonance imaging of macromolecular distribution during infusion. J Neurosurg. 97:905-913, 2002.
14. Mamot C, Nguyen J B, Bankiewicz K S, et al: Extensive distribution of liposomes in rodent brains and brain tumors following convection-enhanced delivery. Journal of Neuro-Oncology 68:1-9, 2004.
15. Mardor Y, Roth Y, Lidar Z, et al: Monitoring response to convection-enhanced taxol delivery in brain tumor patients using diffusion-weighted magnetic resonance imaging. Cancer Res 61:4971-4973, 2001.
16. Morrison P F, Chen M Y, Oldfield E H, et al: Focal delivery during direct infusion to brain: role of flow rate, catheter diameter, and tissue mechanics. Am J Physiol 277: 1218-1229, 1999.
17. Morrison P F, Laske D W, Oldfield E H, et al: High-flow microinfusion tissue penetration and pharmacodnamics. Am J Physiol. 266:292-305, 1994.
18. Nguyen J B, Sanchez-Pernaute R, Cunningham J, et al: Convection-enhanced delivery of MV-2 combined with heparin increases TK gene transfer in the rat brain. Neuroreport 12:1961-1964, 2001.
19. Nicholson C. and Sykova E: Extracelluar space structure revealed by diffusion analysis. Trends Neurosci 21:207-215, 1998.
20. Nicholson C. and Tao L: Hindered diffusion of high molecular weight compounds in brain extracellular microenviroment measured with integrative optical imaging. Biophys J 65:2277-2290, 1993.
21. Oiwa Y, Sanchez-Pernaute R, Bankiewicz K S. et al.: Progressive and extensive dopaminergic degenetration induced by convection-enhanced delivery of 6-hydroxydopamine into the rat striatum: a novel rodent model of Parkinson disease. J Neurosurg 98:136-144, 2003.
22. Saito R, Bringas J R, McKnight T R, et al: Distribution of liposomes into brain and rat brain tumor models by convection-enhanced delivery monitored with magnetic resonance imaging. Cancer Res 64:2572-2579, 2004.

DESCRIPTION OF RELATED ART

Many aqueous substances need to be delivered into the central nervous system (CNS) chronically or acutely for therapeutic or diagnostic reasons. Delivery of such substances is difficult without introducing reflux, introducing air, or being able to accommodate variable brain depths with one device.

The introduction of convection-enhanced delivery (CED) has made the CNS amenable to larger delivery volumes, and consequently is a promising approach for treatment of various diseases located in the CNS that respond poorly to systemic chemotherapy or surgical treatment. CED is a direct intracranial drug delivery technique that utilizes a bulk-flow mechanism to deliver and distribute macromolecules to clinically significant volumes of solid tissues (2, 17, 22). This technique shows a greater volume of distribution compared with simple diffusion and is designed to direct a drug to a specific target site. CED bypasses the blood-brain barrier that is a major obstacle for many systemically applied drugs (2). Several groups have already performed extensive studies to bring CED to clinics (3, 6, 7, 8, 10, 13, 14, 16, 17, 18, 22). Currently CED is used in clinical trials in patients with recurrent glioblastoma multiforme (11, 12, 15).

However, low infusion rate, no standardized catheter design, and reflux are major barriers to broad clinical use in CED at the present time. Low infusion rate is associated with long treatment that is exposing patients to a higher risk of infections, long physical discomfort and emotional stress. The cannula diameter used in clinics, as well as in previous animal studies, allows only a low flow-rate in order to minimize reflux (2, 3, 12, 13, 17). Morrison et al. have already shown in animal experiments that, by reducing diameter of needle (27-32 gauge needle), reflux can be reduced and CED enhanced (16). However, even a 32 gauge needle, one of the smallest metal needles commercially available, is used with a flow rate of 0.5 µl/min to avoid reflux (7, 13, 16). Currently there is no standardized cannula design in CED and catheters with large diameters are used in clinical trials (12). Lidar et al. report that CED led to onset of chemical meningitis during delivery and wound dehiscence after delivery due to leakage of drug in their clinical trial using CED of paclitaxel against malignant gliomas (12). Thus, side effects caused by reflux of delivered agents may limit safe delivery of therapeutic agent.

Additional discussion of CED can be found in the following U.S. patents, U.S. published patent applications, and published PCT patent applications, which are incorporated herein by reference in their entirety:

U.S. Pat. No. 5,720,720
U.S. No. 2003/0045866
U.S. No. 2003/0045861
U.S. No. 2002/0187127
U.S. No. 2002/0141980
U.S. No. 2002/0114780
PCT No. WO 0007652

As can be seen, therefore, clinical application of the convection-enhanced delivery (CED) technique is currently limited by low infusion speed and reflux of delivered agent. Therefore, there is a need for a reflux-resistant cannula which would improve the efficacy of CED. In addition, minimizing the reflux would provide more volume for effective convection and may also allow CED with higher flow rates, which may also improve the therapeutic index of CED and may dramatically reduce the infusion time.

BRIEF SUMMARY OF THE INVENTION

The present invention generally comprises a novel step-design cannula and delivery system for chronic delivery of therapeutic substances into the brain via convection-enhanced delivery (CED). The invention overcomes limitations associated with conventional designs used in CED and provides for a reflux-resistant and fast CED method for future clinical trials. Accordingly, an aspect of the present invention is a reflux-resistant step-design cannula that allows CED with higher flow rates.

Another aspect of the invention is a step-design cannula for human use that comprises a tube having a substantially uniform inner diameter (ID). The outer diameter (OD) of the tube, however, is non-uniform and decreases from the proximal end to distal end in order to minimize damage in brain tissue and ensure reflux safety.

In one beneficial embodiment, a step-design cannula according to the present invention comprises a stainless steel tube having an ID of approximately 0.286 mm (29 gauge) and a length of approximately 234 mm. The OD of the tube is decreases from approximately 5 mm at its proximal end (connection end) to approximately 0.33 mm at its distal end (needle tip) in four steps, thus providing a cannula that has four segments. In this embodiment, the length of the first segment (proximal) is approximately 40 mm with an OD of approximately 5 mm, the length of the second segment is approximately 124 mm with an OD of approximately 2.1 mm, the length of the third segment is approximately 10 mm with an OD of approximately 0.64 mm, and the length of the fourth segment at the distal end (needle tip) is approximately 10 mm with an OD of approximately 0.33 mm. Every change in OD represents a step in the cannula.

Volumes of up to 200 µl trypan-blue with a flow rate of 5, 10 and 20 µl/min were tested in agarose gel to assess reflux resistant delivery and distribution shape associated with the above-described cannula. At 5 µl/min flow rate and 200 µl total volume of delivery a homogenous round shaped distribution was visible around the cannula tip with a stop of backflow at the first step. At 10 µl/min flow rate the round distribution shape started to get irregular and showed disk shape at the bottom part (distal end) of the cannula and round shaped distribution around the upper part of the bottom part of the cannula. At 20 µl/min flow rate, the step-design cannula showed a disk shaped distribution.

Accordingly, the step-design cannula of the present invention can be inserted into the brain at a desired depth for chronic infusion of agents without introducing air or induction of reflux. Magnetic resonance imaging can be performed with this device to assure correct placement and performance of the device. Conventional devices used for brain delivery are not designed for delivery without introduction of air into the tissue or without reflux, both of which reduce the efficacy of CED. The step design of the cannula has the further advantage of significantly reducing reflux and providing for efficient tissue distribution.

In one embodiment, a reflux-resistant cannula for chronic delivery of substances to the brain using CED comprises a tubular member having a proximal end and a distal end; said tubular member having a central lumen between said proximal and distal ends; and an infusion tube positioned in said central lumen and extending beyond said proximal and distal ends; said cannula having an plurality of outer surface segments of varying diameter and length; wherein the diameter of each said outer surface segment is substantially uniform along the length of the segment; wherein the relative diameters of said outer surface segments decreases stepwise from the proximal end to the distal end; and wherein the length and diameter of said outer surface segments are selected to reduce reflux during convection-enhanced delivery of substances into tissue in the brain.

In another embodiment, a reflux-resistant cannula for chronic delivery of substances to the brain via CED comprises a tubular member having a proximal end and a distal end; said tubular member having a central lumen between said proximal and distal ends; and an infusion tube positioned in said central lumen and extending beyond said proximal and distal ends; said cannula having an outer surface with a plurality of stepped segments of varying diameter and length; wherein the diameter of each said stepped segment is substantially uniform along the length of the segment; wherein the relative diameters of said segments decreases stepwise from the proximal end to the distal end; and wherein the length and diameter of said stepped segments are selected to reduce reflux during convection-enhanced delivery of substances into tissue in the brain.

In a further embodiment, a reflux-resistant cannula for chronic convection-enhanced delivery of substances to the brain comprises a tubular member having a proximal end and a distal end; said tubular member having a central lumen between said proximal and distal ends; and an infusion tube positioned in said central lumen and extending beyond said proximal and distal ends; said cannula having an outer surface with a plurality of stepped segments of varying diameter and length; wherein the diameter of each said stepped segment is substantially uniform along the length of the segment; wherein the relative diameters of said segments decreases stepwise from the proximal end to the distal end; wherein said stepped segments comprise a first segment having a length of approximately 40 mm and an outer diameter of approximately 5 mm, a second segment having a length of approximately 124 mm and an outer diameter of approximately 2.1 mm, a third segment having a length of approximately 10 mm and an outer diameter of approximately 0.64 mm, and a fourth segment having a length of approximately 10 mm and an outer diameter of approximately 0.33 mm; and wherein the length and diameter of said stepped segments are selected to reduce reflux during convection-enhanced delivery of substances into tissue in the brain.

In another embodiment, any of the cannula configurations described above includes a central lumen with a substantially uniform inner diameter. In a still further embodiment, at least a portion of the infusion tube is rigid and at least a portion of the infusion tube is non-rigid.

In another embodiment a system for reflux-resistant chronic convection-enhanced delivery of substances to the brain comprises any of the cannula configurations as described above in combination a tubular delivery sheath having an outer surface, a proximal end and a distal end; said delivery sheath having a central lumen extending from said distal end toward said proximal end; said delivery sheath having a longitudinal passageway which communicates between said central lumen and said outer surface; wherein said passageway is configured for insertion of said cannula into said delivery sheath and through said central lumen. In embodiment, the delivery sheath includes a plurality of openings adjacent said passageway configured for receiving sutures.

In one embodiment of the cannula or system, the infusion tube comprises fused silica. In another embodiment, the tubular member is non-rigid. In another embodiment, the infusion tube is non-rigid. In one embodiment of the system, the delivery sheath is non-rigid.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

Figure 2:
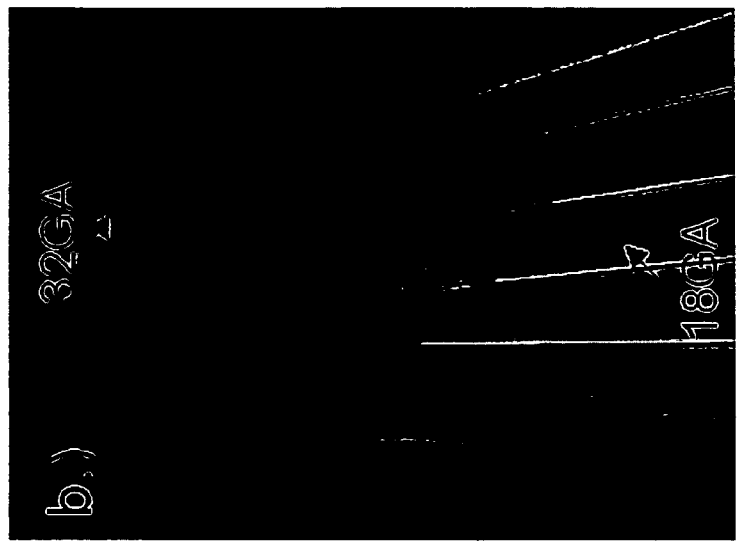
FIG. 2 is a picture showing mm-scale and catheter needles used for delivery of tryptan blue in agarose gel.

FIG. 4A-4H: (4A) 22 gauge catheter needle showing reflux at 0.8 μl/min; (4B) Silica with reflux at 5 μl/min flow rate; (4C) Step-design cannula with silica inside cut at 1 mm from tip (12.5×, 1 mm scale, no infusion performed here); (4D) Step-design cannula (0.5 μl/min flow rate and 10 μl delivery volume); (4E) Step-design cannula (5 μl/min flow rate and 10 μl delivery volume); (4F) Step-design cannula (10 μl/min flow rate and 10 μl delivery volume); (4G) Step-design cannula (20 μl/min flow rate after 10 μl delivery volume); (4H) Step-design cannula (50 μl/min flow rate after 10 μl delivery volume).

Figure 5A:
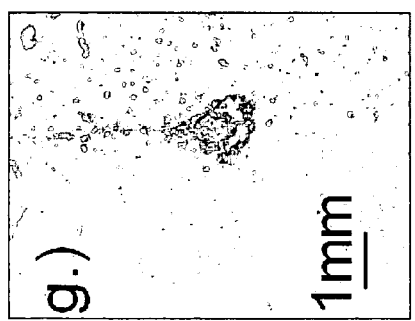

FIG. 5A shows the histology of rodent brains after delivery of 10 μl of trypan-blue with a flow rate of 0.5 μl/min.

Figure 5B:

FIG. 5B shows the damage seen in H&E staining at silica tip with a flow rate of 0.5 g/min.

Figure 6A:
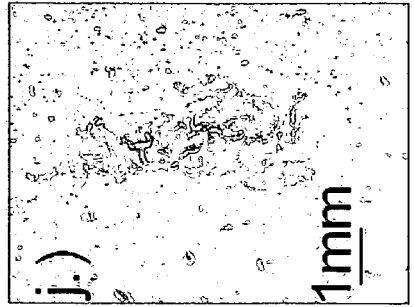

FIG. 6A shows the histology of rodent brains after delivery of 10 μl of trypan-blue with a flow rate of 5 μl/min.

Figure 6B:
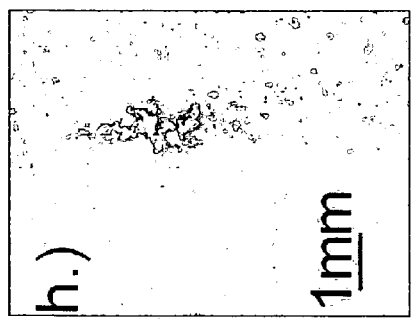

FIG. 6B shows the damage seen in H&E staining at silica tip with a flow rate of 5 μl/min.

Figure 7A:
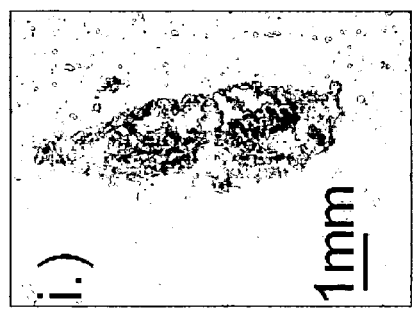

FIG. 7A shows the histology of rodent brains after delivery of 10 μl of trypan-blue with a flow rate of 10 μl/min.

Figure 7B:

FIG. 7B shows the damage seen in H&E staining at silica tip with a flow rate of 10 μl/min.

Figure 8:

FIG. 8 shows the histology of rodent brains after delivery of 10 μl of trypan-blue with a flow rate of 20 μl/min.

Figure 9A:
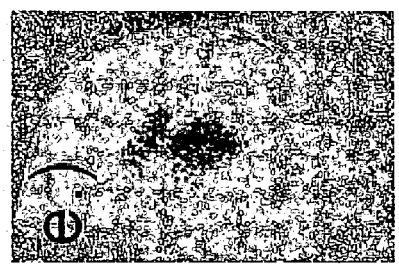

FIG. 9A shows the histology of rodent brains after delivery of 10 μl of trypan-blue with a flow rate of 50 μl/min.

Figure 9B:

FIG. 9B shows the damage seen in H&E staining at silica tip with a flow rate of 50 μl/min.

Figure 10:
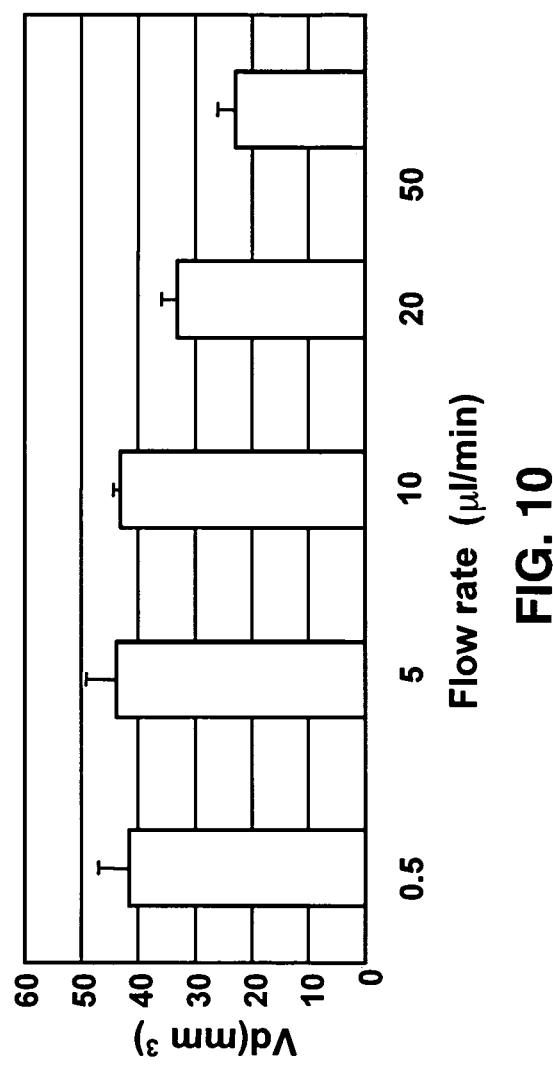

FIG. 10 is a graph showing constant volume of distribution (Vd) from 0.5-10 μl/min flow rate and decreasing Vd at 20 and 50 μl/min (n=4 for each flow rate) for the samples shown in FIGS. 5-9.

FIG. 11A-D is a series of images of the delivery of 10 μl of DiIC$_{18}$-Liposomes into the striatum of rat using 0.5 μl/min flow rate; Regions generating fluorescence were delineated, and those areas were estimated by using NIH Image analysis system.

FIG. 12A-D is a series of images of the delivery of 10 μl of DiIC$_{18}$-Liposomes into the striatum of rat using 5 μl/min flow rate; Regions generating fluorescence were delineated, and those areas were estimated by using NIH Image analysis system.

Figure 13:
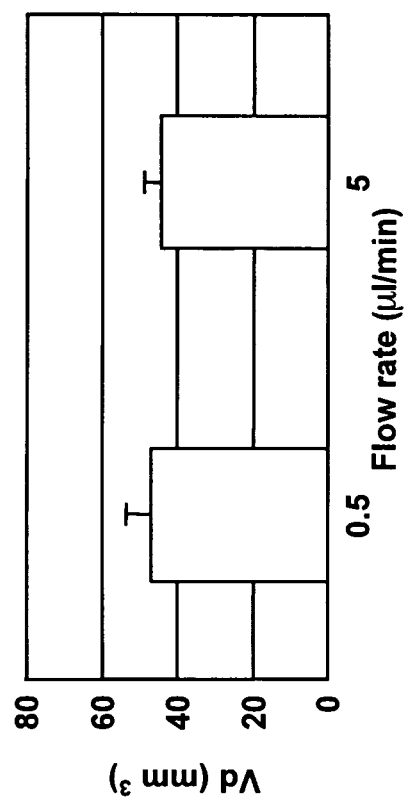

FIG. 13 shows the volume of distribution for 10 μl DiIC$_{18}$-Liposome at 0.5 μl/min (n=5) and 5 μl/min (n=5) flow rate.

Figure 14B:
Figure 14A:

FIG. 14A shows the step-design cannula used in the primate study

FIG. 14B shows the distribution of 100 μl trypan-blue in agarose gel at a 5 μl/min flow rate.

Figure 15:
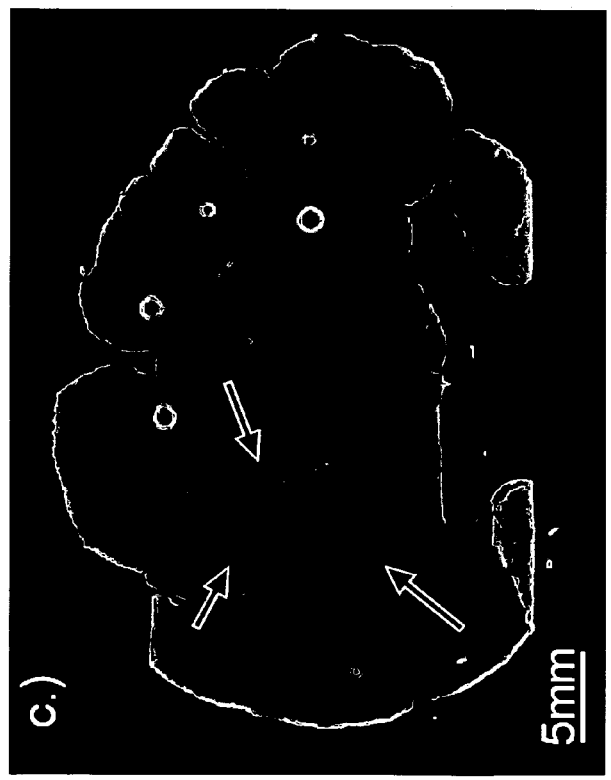

FIG. 15 is an image of the delivery of 99 μl rhodamine liposomes into primate striatum (marked with arrows).

Figure 16:
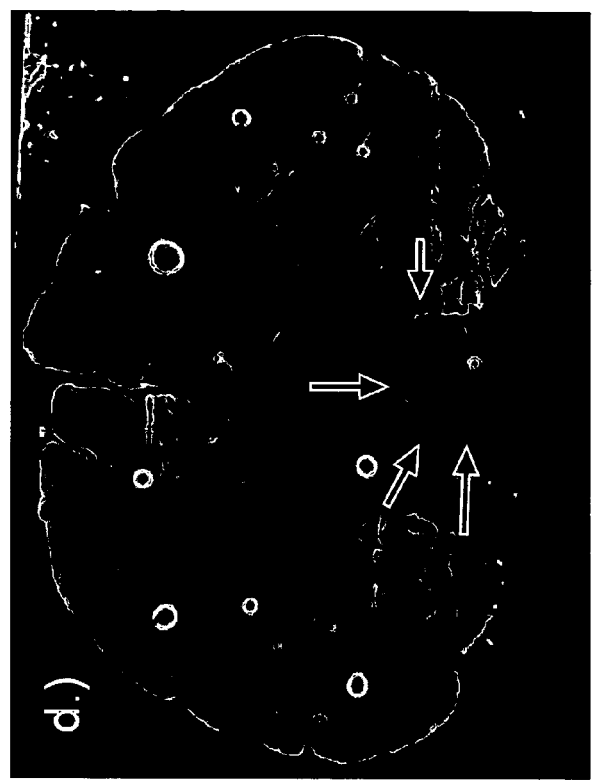

FIG. 16 is an image of the delivery of 66 μl rhodamine liposomes into primate brainstem (marked with arrows).

FIG. 17A-E: (17A) Step-design cannula for human use in clinical CED, each arrow pointing at a step of the cannula, bottom line displays scale equivalent to 1 cm; (17B, 17C) Delivery of 200 μl of trypan-blue in agarose gel with 5 μl/min flow rate; (17D) Delivery of 100 μl of trypan-blue in agarose gel with 10 μl/min flow rate; (17E) Delivery of 100 μl trypan-blue in agarose gel with 20 μl/min flow rate.

Figure 18:
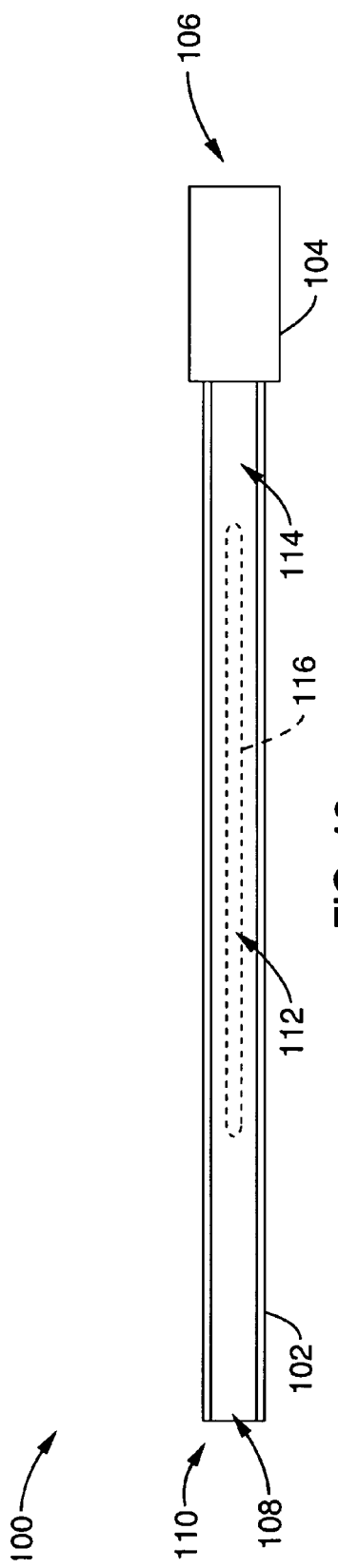

FIG. 18 is a schematic view of an embodiment of a delivery sheath of guiding a step-design cannula according to the present invention into position.

Figure 19:
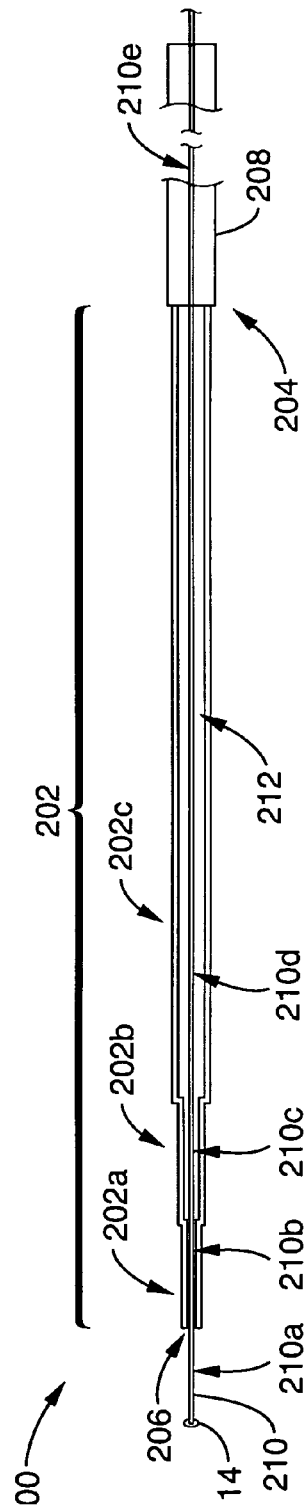

FIG. 19 is a schematic view of an embodiment of a step-design cannula according to the invention configured for chronic convention-enhanced delivery.

Figure 20:
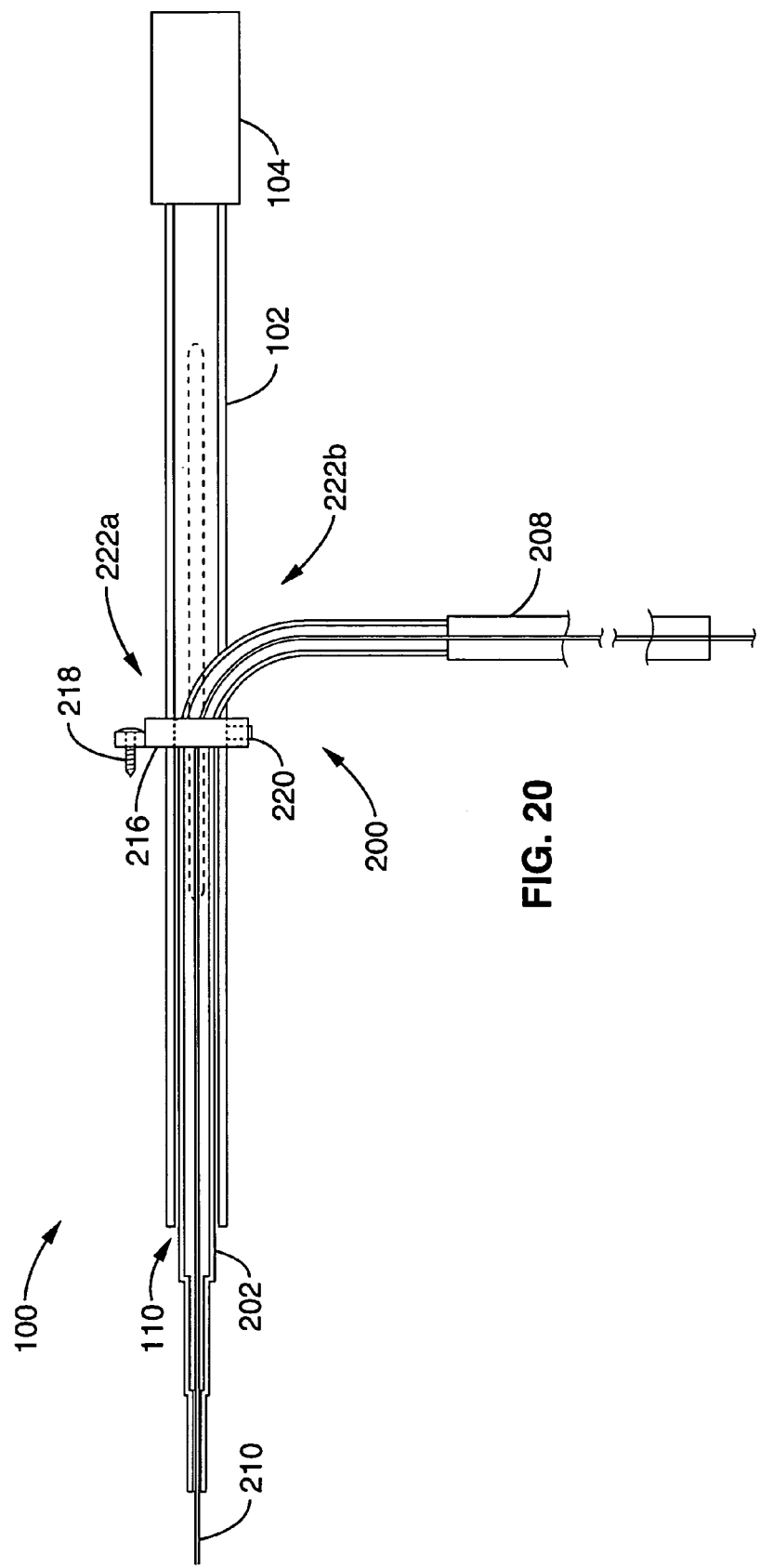

FIG. 20 is a schematic view of an assembly of the delivery sheath showing in FIG. 18 and the cannula showing in FIG. 19 prior to insertion into the brain.

Figure 21:
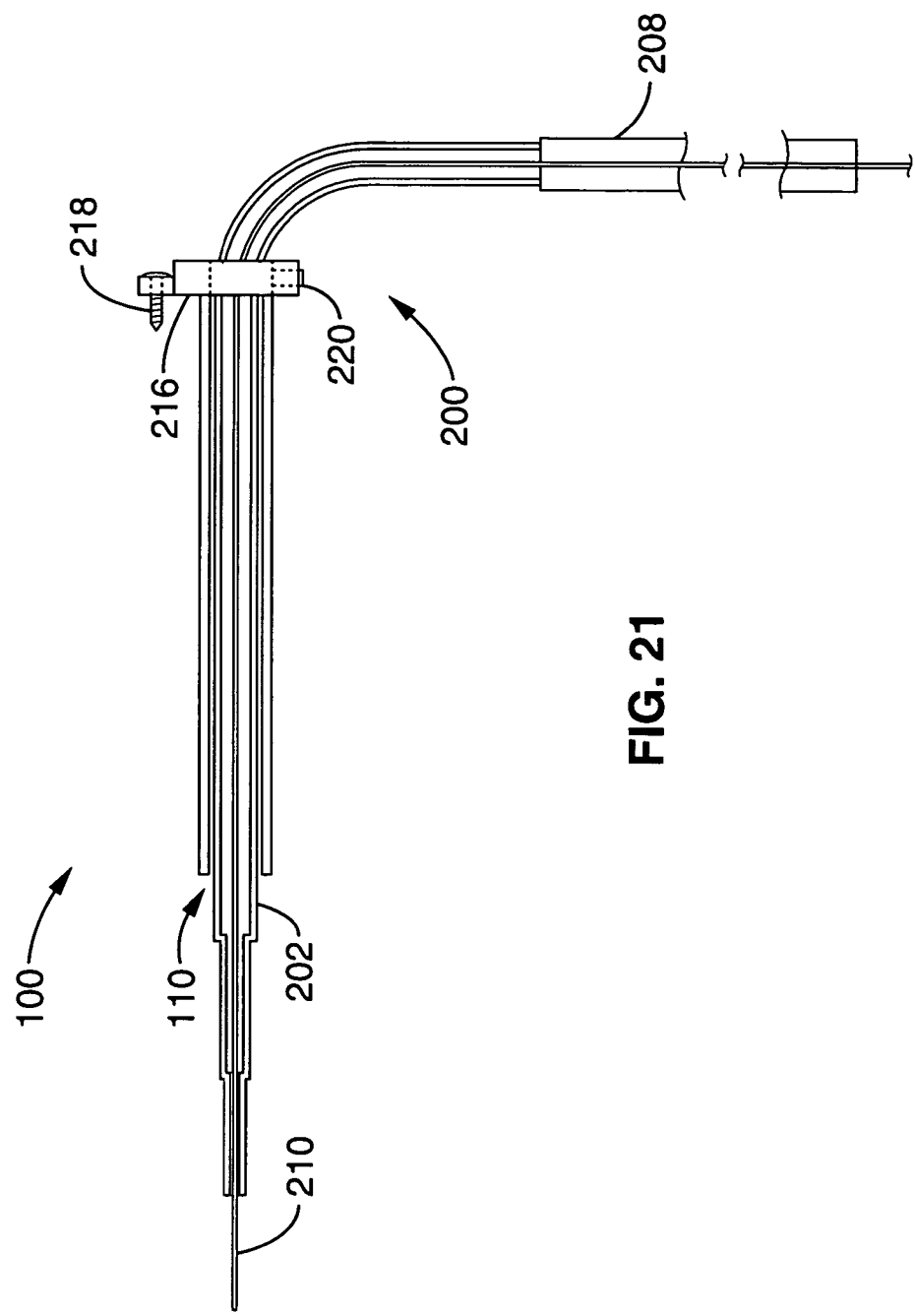

FIG. 21 is a schematic view of the assembly of FIG. 20 after removal of the upper portion of the delivery sheath.

DETAILED DESCRIPTION OF THE INVENTION

Referring more specifically to the drawings, for illustrative purposes the present invention is embodied in the apparatus and methods generally shown with reference to FIG. 1 through FIG. 21. It will be appreciated that the apparatus may vary as to configuration and as to details of the parts, and that the method may vary as to the specific steps and sequence, without departing from the basic concepts as disclosed herein.

Figure 1:
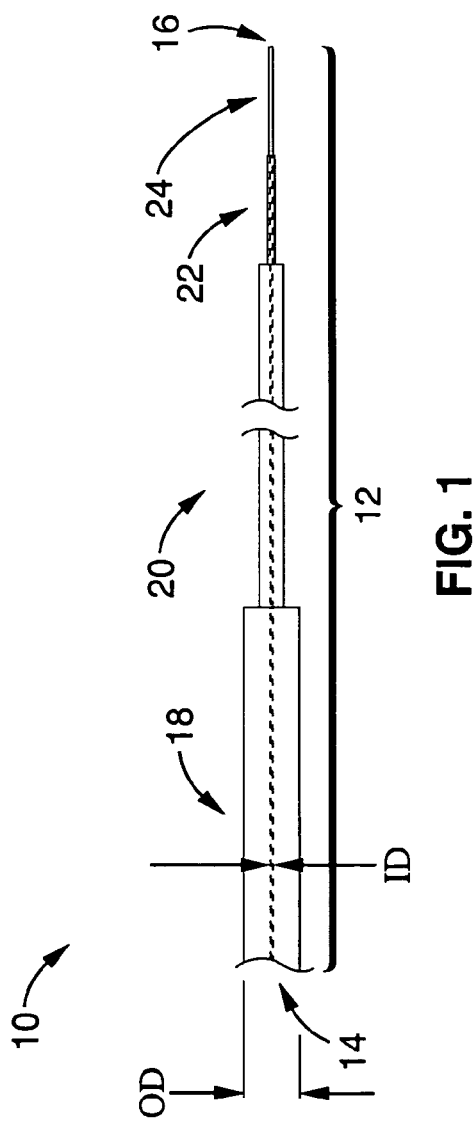
FIG. 1 is a schematic view of an embodiment of a step-design cannula according to the present invention.

Referring first to FIG. 1, the present invention comprises a step-design cannula 10 that addresses the limitations associated with the conventional designs and provides for a reflux-resistant and fast CED method of delivery with higher flow rates than with conventional cannulas.

In the embodiment shown in FIG. 1, cannula 10 comprises a tube 12 having a substantially uniform inner diameter (ID) that defines a central lumen. The outer diameter (OD) of the tube 12, however, is non-uniform and decreases from the proximal end 14 to distal end 16 in order to minimize tissue damage in brain tissue and ensure reflux safety.

In the embodiment of the step-design cannula 10 shown in FIG. 1, the cannula comprises a tube made from titanium or other biocompatible material having an ID of 0.286 mm (29 gauge) and a length of 234 mm. The OD of the tube is decreases from 5 mm at its proximal end 14 to 0.33 mm at its distal end 16 in four steps, thus providing a cannula that has four segments. In this embodiment, the length of the first segment 18 is 40 mm with an OD of 5 mm, the length of the second segment 20 is 124 mm with an OD of 2.1 mm, the length of the third segment 22 is 10 mm with an OD of 0.64 mm, and the length of the fourth segment 24 (needle tip) is 10 mm with an OD of 0.33 mm.

To verify the efficacy of cannula 10 as described above, volumes of up to 200 μl trypan-blue with a flow rate of 5, 10 and 20 μl/min were tested in agarose gel to assess reflux resistant delivery and distribution shape associated with the above-described cannula. At 5 μl/min flow rate and 200 μl total volume of delivery a homogenous round shaped distribution was visible around the cannula tip with a stop of backflow at the first step. At 10 μl/min flow rate the round distribution shape started to get irregular and showed disk shape at the bottom part (distal end) of the cannula and round shaped distribution around the upper part of the bottom part of the cannula. At 20 μl/min flow rate, the step-design cannula showed a disk shaped distribution.

The configuration of the cannula described above is the result of studies and experimentation to prevent reflux that will now be described. Those skilled in the art will appreciate that the particular design and dimensions set forth above represent a beneficial embodiment of the invention and that the overall length, inner diameter, number of steps, and length and outer diameters of the steps can vary without departing from the scope of the invention as taught in the following experimental results and design criteria.

EXAMPLE 1

Agents Infused 0.4% trypan blue solution was purchased from (Sigma, St. Louis, Mo.). All liposomes were prepared by lipid-film hydration using HEPES-buffered saline (pH 6.5) as the hydration buffer. Each sample was hydrated by 6 successive cycles of freezing (−80° C.) and thawing (60° C.). Unilamellar liposomes were formed by extrusion using a 10 ml-capacity thermostatted extruder (Northern Lipids, Vancouver, Canada). Extrusion was performed through polycarbonate membranes using the appropriate pore size and number of extrusions required to reach the desired liposome size (approximately 80 nm), which was determined by light scattering (Beckman Coulter, Fullerton, Calif.). Cholesterol was obtained from Calbiochem (San Diego, Calif.). 1,2-dioleoyl-sn-glycero-3-phosphocholine (DOPC) and 1,2-distearoyl-sn-glycero-3-phosphoethanolamine-N-[methoxy(polyethylene glycol)-2000] (PEG-DSPE) were all purchased from Avanti Polar Lipids (Alabaster, Ala.). All liposomes were composed of a 3:2 (mol:mol) phospholipid/cholesterol mixture. DOPC was used as the phospholipid component and the PEG-DSPE quantity was 10% (mol/mol) of the total phospholipid in this study. $DiIC_{18}$-Liposomes were labeled with membrane-bound $DiIC_{18}$ fluorescence—1,1'-dioctadecyl-3,3,3',3'-tetramethylindocarbocyanine-perchlorate—(Sigma, St Louis, Mo.) having two $C_{18}$ chains. The $DiIC_{18}$ content was 1% (mol:mol) of total phospholipids. Rhodamine liposomes containing sulforhodamine B (Sigma, St Louis, Mo.) were prepared by hydrating the lipid suspension in water-soluble sulforhodamine B (20 mM) and removing unencapsulated dye using a Sephadex G-75 size exclusion column. For all infusion studies, liposomes concentrations were 2 mM phospholipid.

EXAMPLE 2

The Gel Model

We used 0.5% agarose gel (Life Technologies, Gaithersburg, Md.) mixed with PBS for all experiments. All cannulas were fixed with a holder attached to a stereotaxic frame to minimize irregularity (5). The tip of the step-design cannula was placed at the depth of 20-25 mm in the gel and CED with trypan blue was started. Each flow rate for each conventional cannula and each step-design cannula of the present invention was tested at least 4 times to assess reflux. All pictures were taken with a digital camera at the end of the projected delivery time at each flow rate (Canon SD-100, Canon, Lake Success, N.Y.).

EXAMPLE 3

Rodent Study

Male Sprague Dawley rats weighing 250-300 g (Charles River Laboratories, Wilmington, Mass.) were used. The protocol used in these studies was approved by the Institutional Animal Care and Use Committee of the University of California, San Francisco. While under deep isoflurane (Aerrane, Omeda PPD, Liberty, N.J.) anesthesia, rats were placed in a small animal stereotaxic frame (David Kopf Instruments, Tujunga, Calif.). A sagittal incision was made through the skin to expose the cranium, and a burr hole was made in the skull at 0.5 mm anteriorly and 3 mm laterally from the bregma with a small dental drill. Infusions were performed at the depth of 5 mm from brain surface by using the CED method described previously (2, 14, 17). The infusion system consisted of three components: (i) a step-design cannula; (ii) a infusion line containing the infused agent and (iii) a infusion line containing olive oil. The three components were connected using flangeless fittings (Upchurch Scientific, Oak Habour, Wash.) and step-design cannula was attached to stereotaxic frame with a holder. Oil infusion lines were prepared and 1 ml gas tight Hamilton syringes (Hamilton Reno, Nev.) filled with oil were attached to a rate-controllable microinfusion pump (Bioanalytical Systems, Lafayette, Ill.). 10 µl of 0.4% trypan blue solution was used to determine volume of distribution in rat brain. When the step-design cannula reached 5 mm of depth, infusion was immediately started. Flow rates used with trypan blue were 0.5, 5, 10, 20 and 50 µl/min (n=4 for each flow rate). 10 µl of $DiIC_{18}$-liposomes were infused at 0.5 and 5 µl/min (n=5 for each flow rate) using same CED technique as for trypan blue infusion. Infusion cannula remained for another 5 min in position after finishing delivery of trypan blue or $DiIC_{18}$-liposomes. Rats were euthanized immediately after step-design cannula was removed from the skull, and the brains were frozen in dry ice cooled isopentane. Fresh frozen brains were cut into 25 µm thick sections using a cryostat and placed on microscope slides. The volume of distribution was analyzed by using a Macintosh-based image analysis system (NIH Image 1.62; NIH Bethesda, Md.). Hematoxylin and Eosin staining (Richard-Allen Scientific. Kalamazoo, Mich.) of sections was used for evaluation of tissue damage around the cannula tip.

EXAMPLE 4

Non-Human Primate Study

Adult male cynomolgus monkeys (*Macaca fasicularis*, n=3, 2.8-3.5 kg) were assigned to this study. In collaboration with Sierra Biomedical (Sparks, Nev.), a non-human primate study was performed to track the distribution of rhodamine liposomes in targeted regions of the brain. The protocol was reviewed and approved by the Institutional Animal Care and Use Committee at Sierra Biomedical. Animals were individually housed in stainless-steel cage. Animals received intracranial infusion of rhodamine liposomes into putamen and brainstem using convection-enhanced delivery (CED) techniques. The infusion system used for CED was similar to the one used in our rodent study. Each animal was initially sedated with Ketamine (Ketaset; 10 mg/kg, I.M), intubated and prepped for surgery. Isoflurane (Omeda PPD) was delivered at 1-3% to maintain a stable plane of anesthesia. The animal's head was then placed in a stereotaxic frame, and vital signs were continuously monitored during surgery. A bilateral craniotomy was performed using a dental drill to expose a 3 cm×2 cm area of dura mater above the target site (putamen or brain stem). Initial infusion rates were set at 0.1 µl/min; step-design cannulas were fixed with a holder attached to the primate stereotaxic frame and slowly (1 cm/min) lowered to their target sites. An initial infusion rate of 0.2 µl/min was applied and increased at 10-minute intervals to a maximum of 1.5 µl/min. The total infusion volume within each target site was as follows: putamen (99 µl) and brainstem (66 µl). The total infusion time ranged approximately between 70 minutes (to deliver 66 µl) and 90 minutes (to deliver 99 µl). Approximately 15 min following infusion, the step-design cannula assembly was slowly removed out of the cortex. Following completion of the neurosurgical procedure, each animal was euthanized with an overdose of sodium pentobarbital, the brain was harvested and freshly frozen in dry ice cooled isopentane. The tissue was later sectioned (40 µm) using a cryostat, mounted onto slides and targeted regions analyzed for fluorescence generating regions with a Ultra-Violet Transilluminator (Bio-Rad, Hercules, Calif.) for liposome distribution.

EXAMPLE 5

Reflux-Resistant Step-Design Cannula and Human Step-Design Cannula for Clinical Use We used the following cannula design for our animal study: 27 gauge catheter needle (Terumo Medical Corporation, Elkton, Md.) with glued in silica tubing (outer diameter: 168 µm, inner diameter 102 µm) (Polymicro Technologies, Phoenix, Ariz.). The needle with silica inside was glued to tubing that was attached to the CED infusion system (see rodent and non-human primate study discussion below). Silica was cut at 1 mm for rodent and 5 mm for primate studies measured from the catheter needle tip. Reflux was defined as backflow over the step caused by the 27 gauge needle in the rodent and non-human primate study.

The length of the human step-design cannula was 234 mm. The outer diameter of the step-design cannula was reduced from top to bottom as following: Top part length was 40 mm with outer diameter (OD) of 5 mm, second part length was 124 mm with OD of 2.1 mm, third part length was 10 mm with OD of 0.64 mm, and tip length measures 10 mm with OD of 0.33 mm. Every change in OD represents a step in the cannula. The inner diameter of the whole cannula was 0.286 mm (=29 gauge). The top of the device was connected to tubing.

Results

EXAMPLE 6

Agarose Gel Study

Figure 4C:

First, catheter needles with various diameters (18-32 gauge) were taken and the flow rate at which reflux occurs was assessed (FIG. 2,3). Standard catheter needles showed minimal distribution in agarose gel when the threshold of reflux was reached (FIG. 4A). The 32 gauge catheter needle, which is one of the smallest catheter needles commercially available, started to reflux around 5 µl/min flow rate in agarose gel. After reaching the limit in diameter in metal catheter needles, we switched to silica tubing that offers very small diameter at an acceptable level of stability. The flow rate used for silica tubing was 5 µl/min at which infusion with metal needles started to reflux.

Figure 4B:
Figure 4A:
Figure 3:
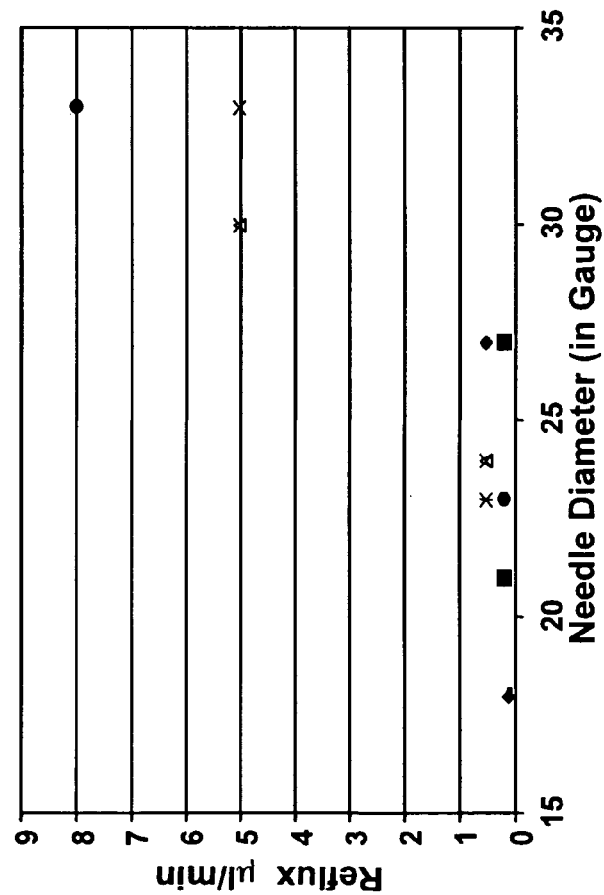
FIG. 3 is a graph showing flow rate (μl/min) of reflux that occurred for each catheter needle diameter (18-32 gauge), shown in FIG. 2, used in agarose gel with delivery of trypan blue.
Figure 4H:
Figure 4G:
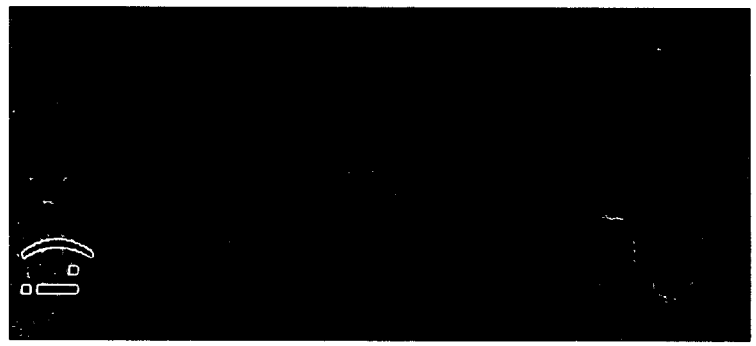
Figure 4F:
Figure 4E:
Figure 4D:
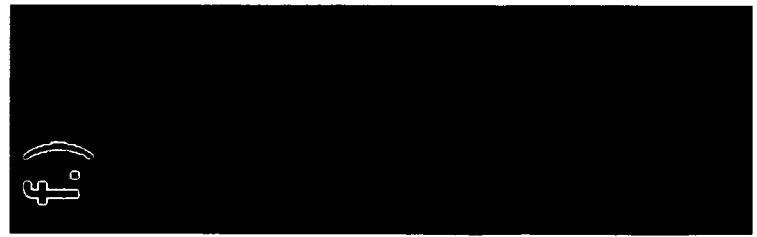

Similarly to the 32 gauge metal needle, the silica tubing (OD: 168 µm, ID: 102 µm) showed reflux at 5 µl/min flow rate as well (FIG. 4B). To make a step-design that might prevent the reflux at its step part, silica tubing was glued into a 27 gauge catheter needle (FIG. 4C). Silica was cut 1 mm distal from the catheter needle tip to adjust our device to rodent brain size. In the next series of studies, reflux was assessed for the new step-design cannula combined with silica tubing. The following flow rates were used for delivery: 0.5, 5, 10, 20 and 50 μl/min with total volume of 10 μl (same volume as used in rodent study) of trypan blue in agarose gel (FIG. 4D-H). Delivery time lasted 20 min at a flow rate of 0.5 μl/min, 2 min at 5 μl/min, 1 min at 10 μl/min, 30 sec at 20 μl/min and 12 sec at 50 μl/min. No reflux occurred with the new step-design cannula. The shape of distribution of trypan-blue was ball shaped from 0.5 μl to 5 μl/min, started to become irregular at 10 μl/min and totaling in a disk-shape at 20 and 50 μl/min. Reflux in the agarose study for the rodent step-design cannula would be defined as backflow of dye over the cannula step caused by the 27 gauge needle.

EXAMPLE 7

Distribution of Trypan-Blue and DiiC$_{18}$-Liposomes in Rodent Brain

Based on the findings from the agarose gel study, a rodent experiment was set up. Flow rates used were same as in agarose gel study and were the following 0.5, 5, 10, 20 and 50 μl/min with same delivery time as used in agarose gel. Each rat (n=20) was infused 10 μl of trypan blue into each hemisphere to assess volume of distribution (Vd) and possible reflux in rodent brain. The new step-design cannula showed no sign of reflux in the rodent brain during delivery rates of 0.5, 5, 10, 20 and 50 μl/min. After finishing delivery at 20 and 50 μl/min and leaving the step-design cannula for 5 min in position, small amounts of trypan blue were seen to drain to the surface when removing the cannula after this time. Histological examination revealed difference in damage at the area surrounding the step-design cannula tip revealed difference in damage depending on flow rate used. Minimal tissue damage due to cannula tract were found at 0.5 and 5 μl/min flow rate, whereas much larger area of damage was detected in the brain received flow-rate from 10 to 50 μl/min. See FIGS. 5-9.

Vd was almost constant from 0.5 μl/min to 10 μl/min flow rate (mean 42.8 mm$^3$), showing decrease at 20 μl/min (mean 32.9 mm$^3$) and remarkable decrease at 50 μl/min (mean 22.7 mm$^3$) (see table in FIG. 10).

Subsequently, 10 μl DiIC$_{18}$-liposomes were infused at a low flow rate of 0.5 μl/min (FIG. 11A-D) and high flow rate of 5 μl/min into the rodent striatum (FIG. 12A-D). Results obtained show similar Vd for 0.5 μl/min (46.3 mm$^3$/SD: 6.6 mm$^3$) and 5 μl/min (43.5 mm$^3$/SD: 4.2 mm$^3$) (FIG. 13). No fluorescence was detected on the surface of brain or along the upper needle track in histology slides.

EXAMPLE 8

Non-Human Primate Liposome Delivery

The step-design cannula used in the non-human primate study was adjusted to brain size by cutting silica 5 mm distal to needle tip (FIG. 14A). Reflux resistant delivery of 100 μl trypan-blue at 5 μl/min flow rate was performed in agarose gel prior to the study to confirm reflux-safety of our device (FIG. 14B).

A reflux-resistant and targeted delivery of 99 μl rhodamine liposomes was performed into striatum (FIG. 15). Similar reflux-resistant infusion was achieved after delivery of 66 μl rhodamine liposomes into brainstem (FIG. 16). Maximal flow rate used for delivery to both locations was 1.5 μl/min. Despite the anatomical heterogeneity of non-human primate brain, our step-design cannula showed reflux-resistant delivery into different depths and regions of brain.

EXAMPLE 9

Human Step-Design Cannula

Figure 17C:
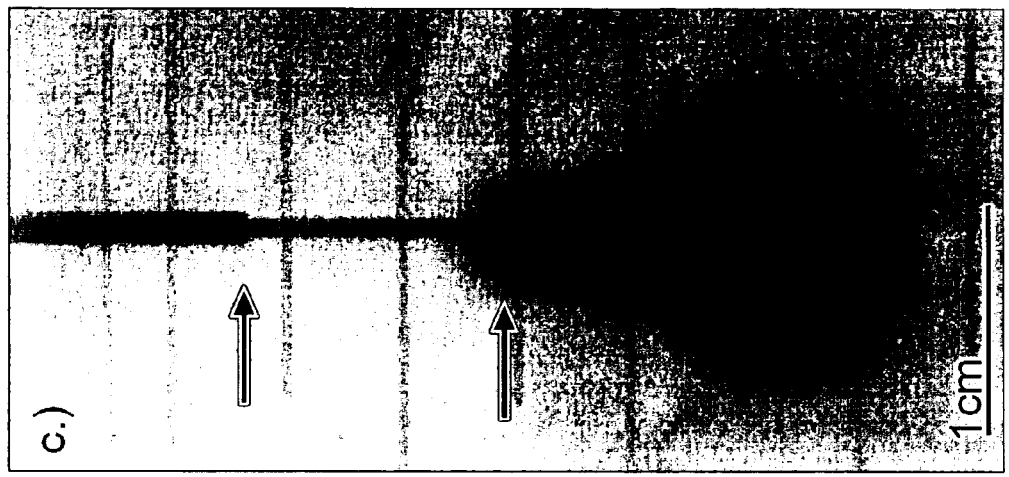
Figure 17B:
Figure 17A:
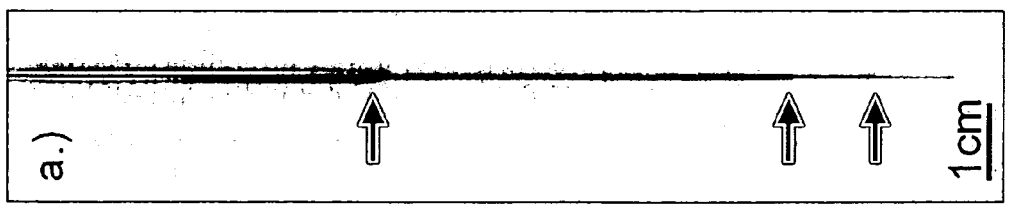
Figure 17E:
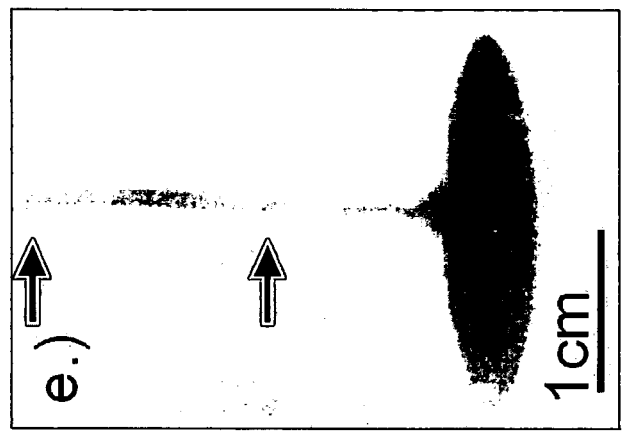
Figure 17D:
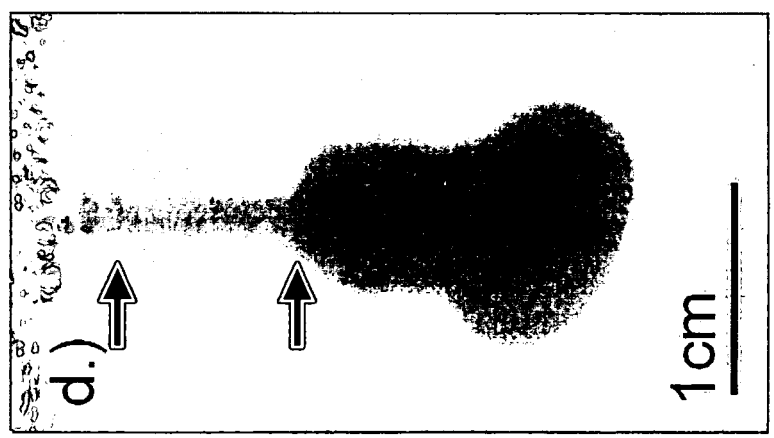

All findings gathered in the agarose gel and animal studies led to development of a human step-design cannula for future use in clinics. The cannula design contains four steps in order to minimize tissue damage in brain tissue and to assure reflux safety (FIG. 17A). The outer diameter is reduced from 5 mm at the top to 0.33 mm at the needle tip. In this much larger metal catheter design, the silica tip was cut at 10 mm from the distal (needle end). Volumes of up to 200 μl of trypan-blue with flow rates of 5, 10 and 20 μl/min were tested again in agarose gel to assess reflux resistant delivery and distribution shape (FIG. 17B-E). At a 5 μl/min flow rate and 200 μl total volume of delivery, a homogenous round shaped distribution was visible around the cannula tip with a stop of backflow at the first step (FIG. 17B, 17C). At a 10 μl/min flow rate round distribution shape started to get irregular and showed disk shape at the bottom part of the cannula and round shaped distribution around the upper part of the bottom part of the cannula (FIG. 17D). At a 20 μl/min flow rate our human step-design cannula showed disk shaped distribution (FIG. 17E).

Discussion

The agarose gel study evaluating reflux rate of catheter needle/cannulas of different diameters confirmed findings from previously reported rodent studies that a smaller diameter allows higher flow-rate in CED (16). The commercially available smallest 32 gauge catheter needle, as well as even smaller silica, started to reflux around 5 μl/min flow rate in agarose gel. This suggested the present limit for catheter design in CED. However, our novel reflux-resistant step-design cannula showed reflux-resistant delivery up to 50 μl/min flow rate in agarose gel. This in turn enhanced CED and consequently shortened time needed to deliver a certain volume. This step-design cannula also enabled reflux-resistant effective delivery of dyes and liposomes in rodent and also in non-human primate brains. However, another limitation for CED was found in rodent brains that were the increasing tissue damage at the needle tip in rodent brain at high flow rates. From the rate of 10 μl/min, which was the rate shape of distribution started to get irregular in agarose gel studies, tissue damages were observed at the cannula tip. In the rodent brain, robust distribution of trypan blue was achieved until the flow rate of 10 μl/min; however, the distribution volume decreased above this rate. The drainage of trypan blue to the surface of rodent brain seen after the removal of our step-design catheter at 20 and 50 μl/min strongly suggests that this high delivery speeds exceed convection in brain tissue leading to a decreased volume of distribution and tissue damage. This finding also suggests that our step-design cannula is a tight seal during delivery. From another observation that strengthens this hypothesis, we believe that the irregular and disk shaped distribution of trypan blue in agarose gel was a reflection of irregular and high pressure build up and therefore at these flow rates tissue damages were observed in rodent brains. This is reasonable because, in case of intracerebral hemorrhage, high pressure of the blood leaking from the collapsed vasculature destroy the surrounding brain tissue by pressing normal brains aside. Similar observations were made using the human cannula we created. At the flow rate of 10 μl/min, the distribution shape of trypan blue became irregular. This might suggest that independent of the cannula size, a flow rate in excess of 10 μl/min may cause tissue damage.

Once the reflux occurs, the problem is not only ineffective tissue damage. Compared with our step-design cannula, the distribution of a refluxing catheter needle is greatly minimized by dye draining to the surface of the agarose gel. This finding strongly implicates that some side effects seen in clinical trials are due to drainage of fluid to the surface of the brain (12). Because of this reason reflux must be avoided when applying CED into clinical studies using cytotoxic agents. In this study we demonstrated reflux-resistant effective delivery of liposomes that we recently focusing as a carrier for CED mediated drug delivery (14, 22) in rodent brains and also non-human primate brains using our step-design cannula. Our maximal rate that enabled effective and safe delivery was not different from that used in recent clinical trials (<5 μl/min). In clinical trials, this flow rate results in a duration lasting several hours to days to deliver clinically significant volumes, i.e. 72 ml, by CED into targeted site (11). However, due to likelihood of reflux in current trials, the total volume delivered at the targeted side is not predictable. Thus we believe that reflux-resistant CED at this flow rate might enhance the efficacy of CED and therefore reduce the infusion volume that is required to cover target structure and in turn shorten the duration of CED.

Since our group is developing a clinical trial using CED for Parkinson's disease, we developed a cannula for human application (1, 6, 18, 21). In the agarose gel study it demonstrated results similar to the rodent cannula. The step-design worked to prevent reflux and symmetrical ball-shape distribution was observed until the rate of 5 μl/min; however, higher than 10 μl/min showed a tendency to make disk-shaped distribution. We believe that this catheter design may improve the efficacy of CED also in clinical trials and make CED more reliable and easier technique to perform. Future study addressing the correlation between volume of infusion and volume of distribution may prove the importance of non-reflux catheter we developed.

Referring now to FIG. 18 through FIG. 21, an embodiment of a reflux-resistant cannula system for chronic delivery of therapeutic substances into the brain is illustrated. In the embodiment shown, the system generally comprises a delivery sheath 100 and a step-design infusion cannula assembly 200, where the delivery sheath 100 functions as a guide component for the infusion cannula 200 to assist placement of the infusion cannula for chronic attachment to the skull. The system would be used in combination with an infusion pump that is either externally or subcutaneously placed.

FIG. 18 shows an embodiment of a delivery sheath 100 that comprises a tubular member 102 which has, at one end, a coupling 104 that is adapted to be connected to a stereotaxic frame for support and placement. The tubular member 102 is preferably fabricated from a non-ferromagnetic flexible material such as a biocompatible plastic or a metal such as titanium. The coupling 104 is a conventional coupling that is adapted for connection to a stereotaxic frame at its proximal end 106. The connection between tubular member 102 and coupling 104 can be made using a conventional biocompatible bonding technique such as gluing the components together.

A central lumen 108 runs through at least a portion of tubular member 102 for receiving an infusion cannula of the type described herein. Accordingly, the inner diameter of central lumen 108 would typically be larger than the largest outer diameter of cannula 200 that will be inserted through the lumen. The distal end 110 of tubular member 102 is open so that the infusion cannula can extend therethrough. A longitudinal passageway or slot 112 communicates between the outer surface 114 of the tubular member and the central lumen for insertion of the infusion cannula into the delivery sheath. A plurality of openings 116 are positioned adjacent the perimeter of passageway 112 though which sutures can be placed.

FIG. 19 illustrates an embodiment of an infusion cannula 200 for use with delivery sheath 100. Except as noted in the following discussion, infusion cannula 200 has the same multiple-step configuration previously described. In the embodiment shown, infusion cannula 200 comprises a tubular body 202 having a substantially uniform inner diameter (ID). The outer diameter (OD) of the tubular body 202, however, is non-uniform and decreases from the proximal end 204 to distal end 206.

In one embodiment of the step-design infusion cannula 200 shown in FIG. 19, the tubular body 202 is fabricated from a synthetic MRI-compatible and biocompatible material. Examples of suitable materials include biocompatible plastics, metals such as titanium, and fused silica. In the embodiment shown in FIG. 19, tubular body 202 has three steps 202a, 202b and 202c, but the number of steps can vary without losing functionality. Preferably, the two steps 202a, 202b adjacent distal end 206 are fabricated from fused silica, titanium or the like for rigidity. However, step 202c is preferably fabricated from a flexible biocompatible material which can be bent as illustrated in FIG. 20 and FIG. 21. A tubing 208 is coupled to the proximal end of the tubular body 202, and is preferably fabricated from a flexible biocompatible material since the tubing is intended to be tunneled under the skin of the patient and ultimately connected to an infusion pump. The connection between tubing 208 and the tubular body 202 can be made using a conventional biocompatible bonding technique.

An infusion tube 210, preferably fabricated from fused silica, is positioned in the central lumen 212 of the tubular body 202 and represents the smallest diameter in the infusion cannula 200. Infusion tube 210 extends through tubing 208, through tubular body 202, and past the proximal end 206 of tubular body 202 for delivery of a therapeutic agent into the brain. Tubing 208 provides protection for infusion tube 210 between infusion cannula 200 and the infusion pump. Referring to FIG. 1, it can be seen that the portion of infusion tube 210 that extends beyond proximal end 206 of tubular body 202 is equivalent to step 24 in cannula 10. More particularly, the cannula 10 shown in FIG. 1 is an integral unit having four steps, whereas the cannula 200 shown in FIG. 19 is a two component cannula. One component, which provides three steps, is tubular body 202. The fourth step, which serves as the delivery tip, is formed by infusion tube 210 which runs through the central lumen in tubular body 202. Accordingly, in one embodiment, infusion tube 202 would extend beyond the distal end 206 of tubular body 202 by approximately 10 mm and the inner diameter of tubular body 202 would approximately match the outer diameter of infusion tube 210 (e.g., 0.33 mm).

If desired, a ferrous magnetic bead 214 or the like can be attached to infusion tube 210 as illustrated to facilitate placement using a neuro-navigation system for frame-less stereotaxic surgery. In this embodiment, the neuro-navigation system would be used as an alternative to using a stereotaxic frame. In that event, the coupling 104 on delivery sheath 100 shown in FIG. 18 could be eliminated. Still another alternative to using a stereotaxic frame is to use a laser to measure distance to determine depth of placement of the cannula.

In one beneficial embodiment of infusion cannula 200, infusion tube 210 comprises multiple segments to facilitate bending and placement as illustrated in FIG. 20 and FIG. 21. As discussed above, body segment 202c is preferably fabricated from a flexible material to allow for bending. However, such bending could possibly damage the portion of infusion tube 210 that runs through body segment 202c. Accordingly, the portion of infusion tube 210 that runs through body segment 202c could be fabricated from a flexible material. For example, infusion tube segment 202d could comprise a flexible material such as Teflon® while infusion tube segments 210a, 210b, 210c and 210e would comprise fused silicon. In this embodiment, infusion tube segment 202d would be bonded, such as by means of gluing, to the proximal and distal fused silicon segments. In a further beneficial embodiment, infusion tube segment 202e would also comprise a Teflon® tube. In still another beneficial embodiment, central lumen 212 could be a non-uniform diameter or have a diameter larger than infusion tube 210, in which case the "dead space" between infusion tube 210 and the inner wall of body 202 would be filed or packed with a material such as adhesive material to fill the "dead space".

FIG. 20 shows the delivery sheath 100 and infusion cannula 200 in an assembled system configuration. In FIG. 20, the two components are shown positioned generally as they would prior to insertion into the brain. As can be seen, the proximal end 110 of the delivery sheath 100 functions as the most external segment of the step-design of the infusion cannula, thus increasing the overall number of steps in the step-design. Accordingly, a total of five steps are shown in FIG. 20.

Note also from FIG. 20 that use of a flexible material for tubular body 202 allows for bending of infusion cannula 200 in relation to delivery sheath 100. Accordingly, delivery sheath 100 can be used for positioning infusion cannula 200 in the brain and the proximal end of infusion cannula 200 with tubing 204 can be tunneled under the skin in a compact manner. Tubing 208 and infusion tube 210 typically would be connected to the infusion pump before insertion of the assembly into the brain. Then, before insertion, infusion would be initiated to fill the infusion tube 210 with infusate to purge air from infusion tube 210. It should be noted that purging prior to insertion is an important step since purging after insertion will create an air pocket and inhibit convection.

Once delivery sheath 100 and cannula 200 are placed at the proper depth, the assembly is fixed in position. This can be accomplished by, for example, using an o-ring shaped holding bracket 216 through which a bone screw 218 is inserted to rigidly attach the holding bracket to the skull. A set screw 220 would then be used to lock delivery sheath 100 and cannula 200 in position to prevent relative movement. In this way, the holding bracket 216, delivery sheath 100 and cannula 200 are fixedly coupled to each other. In another beneficial embodiment, the set screw 220 can be eliminated and delivery sheath 100 and cannula 200 held together using sutures.

Referring also to FIG. 21, after the assembly is positioned, the upper portion of delivery sheath 100 is removed by cutting the sheath just above the points 222a, 222b where infusion cannula 200 bends over. Prior to doing so, however, silk suture material is preferably placed through the small openings 116 just below the cut line defined between points 222a and 222b and tied to the holding bracket 216 to affix the assembly in place. The skin can then be closed within the anatomical layers.

Note that the flexibility of the components allows for movement with the brain. Note also that there is a high degree of adjustability in the assembly which allows for the depth of placement to be varied. For example, the longitudinal passageway 112 in delivery sheath 100 not only allows for insertion of cannula 200 into that component but also allows for cannula 200 to be adjusted in position longitudinally in relation to proximal end 106 and distal end 110. In addition, the position of the assembly can be adjusted relative to the holding bracket 216 which is attached to the skull. To facilitate depth of placement, the external surface of tubular body 202 can be calibrated with scale markings (e.g., using a mm scale) if desired.

CONCLUSIONS

Improvement of current CED methods is the key for a broad clinical availability. The results of our work show drastic improvement of methods in CED. We believe that our findings represent a reflux resistant and faster method to improve current CED protocol that will lead to broad clinical availability in the near future.

Thus far we have described a reflux-resistant cannula and system for chronic CED of therapeutic substances into the brain. We have also described a reflux-resistant cannula for acute CED use. U.S. Published Application No. US2006/0135945 A1, published Jun. 22, 2006, incorporated herein by reference in its entirety, provides additional background and design criteria which can be applied to the cannulas described herein. Sanftner et al., "AAV-2-mediated gene delivery to monkey putamen: Evaluation if an infusion device and delivery parameters", Exp. Neurol., Vol. 194, pp. 476-483 (2005), incorporated herein by reference in its entirety, provides additional background and design criteria which can be applied to the cannulas described herein, as well as additional test results relating to the step-design cannula.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A reflux-resistant cannula for chronic convection-enhanced delivery of substances to the brain; the cannula comprising:
   a tubular body having a proximal end and a distal end and having a central lumen between said proximal and distal ends, wherein the proximal portion of said tubular body is non-rigid; and an infusion tube positioned in said central lumen and extending beyond said proximal and distal ends of said tubular body, wherein the portion of said infusion tube extending beyond said distal end of said tubular body forms a rigid delivery tip of fixed length and having a smaller diameter than the distal end of said tubular body, and wherein the portion of said infusion tube extending beyond said proximal end of said tubular body is non-rigid;

wherein during convection-enhanced delivery of substances into tissue in the brain said cannula shows no backflow beyond said delivery tip at flow rates up to 10 μl/min.

2. A cannula as recited in claim 1, wherein the distal end of said infusion tube is fused silica.

3. A system for reflux-resistant chronic convection-enhanced delivery of substances to the brain, comprising:

a cannula according to claim 1; and a tubular delivery sheath having an outer surface, a proximal end and a distal end;

said delivery sheath having a central lumen extending from said distal end toward said proximal end;

said delivery sheath having a longitudinal passageway which communicates between said central lumen and said outer surface wherein said delivery sheath includes a plurality of opening adjacent said passageway configured for receiving sutures;

wherein said passageway is configured for insertion of said cannula into said delivery sheath and through said central lumen.

4. A system as recited in claim 3, wherein the distal end of the infusion tube is fused silica.

5. A system as recited in claim 3, wherein at least a portion of said delivery sheath is non-rigid.

6. A system as recited in claim 3, wherein said tubular body has a substantially uniform inner diameter of approximately 0.33 mm.

7. The system as recited in claim 3, wherein said rigid delivery tip is approximately 1 mm to 10 mm in length.

8. The cannula of claim 1, wherein the inner diameter of said tubular body approximately matches the outer diameter of said delivery tip.

9. The cannula of claim 1, wherein said delivery tip is decreased in diameter from 0.31 to 1.77 mm relative to said tubular body.

10. The cannula of claim 1, wherein said delivery tip is decreased in diameter approximately 0.31 mm relative to said tubular body.

11. The cannula of claim 1, wherein the outer diameter of said tubular body is non-uniform and decreases from the proximal end to the distal end.

12. The cannula as recited in claim 11, wherein said tubular body comprises a first segment having a length of approximately 40 mm and an outer diameter of approximately 5 mm, a second segment having a length of approximately 124 mm and an outer diameter of approximately 2.1 mm, and a third segment having a length of approximately 10 mm and an outer diameter of approximately 0.64 mm; and wherein said infusion tube extends beyond said third segment by approximately 10 mm to form said delivery tip and has an outer diameter of approximately 0.33 mm.

13. The cannula as recited in claim 1, further comprising a tubing fabricated from a flexible biocompatible material coupled to the proximal end of said tubular body.

14. The cannula as recited in claim 1, wherein said rigid delivery tip is approximately 1 mm to 10 mm in length.

\* \* \* \* \*